United States Patent [19]
Driehuys et al.

[11] Patent Number: 5,612,103
[45] Date of Patent: Mar. 18, 1997

[54] COATINGS FOR PRODUCTION OF HYPERPOLARIZED NOBLE GASES

[75] Inventors: Bastiaan Driehuys, Bristol, Pa.; William Happer, Princeton; Gordon D. Cates, Jr., Skillman, both of N.J.

[73] Assignee: Princeton University, Princeton, N.J.

[21] Appl. No.: 478,276

[22] Filed: Jun. 7, 1995

[51] Int. Cl.$^6$ .................................................. A47G 19/22
[52] U.S. Cl. ..................... 428/34.7; 427/294; 428/429; 528/31
[58] Field of Search .................. 427/385.5, 387, 427/294; 528/31; 428/34.7, 429

[56] References Cited

U.S. PATENT DOCUMENTS

| | | | |
|---|---|---|---|
| 3,642,851 | 2/1972 | Bennett | 260/448.2 N |
| 3,646,090 | 2/1972 | Bennett | 260/448.2 E |
| 3,657,363 | 4/1972 | Dorko | 260/642 |
| 3,966,781 | 6/1976 | Atkinson et al. | 260/410.9 R |
| 3,989,705 | 11/1976 | Werstiuk et al. | 260/290 P |
| 4,586,511 | 5/1986 | Clark, Jr. | 128/653 |
| 4,882,384 | 11/1989 | Willis et al. | 525/366 X |
| 4,914,160 | 4/1990 | Azizian | 525/329.3 |

OTHER PUBLICATIONS

Mohr JM and Paul DR "Surface fluorination of composite membranes. Part I. Transport properties", *Journal of Membrane Science*, 55 (1991) 131–148.

Le Roux JD, Teplyakov VV and Paul DR "Gas transport properties of surface fluorinated poly(vinyltrimethyl–silane) filmes and composite membranes", *Journal of Membrane Science*, 90 (1994) 55–68.

Bouchiat MA and Brossel J "Relaxation of Optically Pumped Rb Atoms on Paraffin–Coated Walls", *Physical Review 147*, No. 1, 8 Jul. 1966.

Zeng X, Miron E, Van Wijngaarden WA, Schreiber D and Happer W. "Wall Relaxation of Spin Polarized $^{129}$Xe Nuclei", *Physics Letters*, 96A (4), 27 Jun. 1983.

Cates GD, Benton DR, Gatzke M, Happer W, Hasson KC and Newbury NR "Laser Production of Large Nuclear–Spin Polarization in Frozen Xenon" 65 (20), 12 Nov. 1990.

Miller JB, "$^{129}$Xe NMR in Polymers" *Rubber Chemistry and Technology 66*, 455 (1993).

Wu Z, Happer W, Kitano M and Daniels J "Experimental studies of wall interactions of adsorbed spin–polarized $^{131}$Xe nuclei" *Physical Review A 42* (5) 1 Sep. 1990.

Cain EJ, Wen WY, Jost RD, Liu X, Dong ZP, Jones AA and Inglefield PT, "Nuclear Spin Relaxation Mechanisms and Mobility of Gases in Polymers" *J. Phys. Chem.* 94 2128–2135 (1990).

*Primary Examiner*—Michael Lusignan
*Attorney, Agent, or Firm*—Hoffmann & Baron

[57] ABSTRACT

The invention provides a method of inhibiting surface-induced nuclear spin relaxation and surface trapping of a hyperpolarized noble gas, most preferably $^{129}$Xe, by polymer-coated surfaces. The method includes inhibiting the amount of interaction of the noble gas with a polymeric coating on the surface of apparatus which contacts the noble gas. Preferably, the method includes inhibiting noble gas nuclear spin relaxation by replacing at least some of the protons in the polymer with substituents which have non-zero nuclear spin and/or reduced polymer permeability. A preferred substituent having non-zero spin is deuterium. A preferred modification which reduces permeability includes introducing into the polymer a substituent such as a halogen, more preferably fluorine. The method also provides containers having surfaces which have been coated with a polymer which inhibits noble gas trapping and nuclear spin relaxation. Furthermore, the invention provides methods for enhancing the production and storage of a hyperpolarized noble gas by decreasing the relaxation of nuclear spin and limiting the trapping of the noble gas in a polymeric coating of apparatus containing the noble gas.

47 Claims, 4 Drawing Sheets

COATINGS FOR PRODUCTION OF HYPERPOLARIZED NOBLE GASES

This invention was made with Government support under Grant No. F49620-92-J-0211 awarded by the Air force Office of Scientific Research and under Grant No. DAAH04-94-G-0204 awarded by the Army Research Office. The Government has certain rights in this invention.

BACKGROUND OF THE INVENTION

This invention relates to methods of inhibiting nuclear spin relaxation of hyperpolarized noble gas. More particularly, the invention relates to a method of inhibiting depolarizing interactions of hyperpolarized $^{129}$Xe with a polymeric coating on a surface.

The number and variety of applications of noble gases, particularly $^3$He and $^{129}$Xe, polarized through spin-exchange optical pumping (Bhaskar N D, Happer W, and McClelland T, *Phys Rev Lett* 49:25 (1982); Happer W, Miron E, Schaefer S, van Wijngaarden, and Zeng X, *Phys Rev A* 29:3092 (1984)) have grown rapidly over the past few years. Most recently, the enhanced NMR signals of laser-polarized $^{129}$Xe, which are about five orders of magnitude larger than those from thermally polarized $^{129}$Xe, have made possible the first high-speed biological magnetic resonance imaging (MRI) of a gas (Albert M S, Cates G D, Driehuys B, Happer W, Saam B, Springer C S, and Wishnia A, *Nature* 370:188 (1994)), opening many new avenues of research. Historically, polarized $^{129}$Xe has been used for fundamental symmetry studies (Chupp T E, Hoare R J, Walsworth R L, and Wu B, *Phys Rev Lett*, 72:2363 (1994)), nuclear spin relaxation studies of solids. (Gatzke M, Cates G D, Driehuys B, Fox D, Happer W, and Saam B, *Phys Rev Lett*, 70:690 (1993)), high resolution nuclear magnetic resonance spectroscopy (NMR) (Raftery D, Long H, Meersmann T, Grandinetti P J, Reven L, and Pines A, *Phys Rev Lett*, 66:584 (1991)), and cross-polarization to other nuclei (Gatzke et al., *Phys Rev Lett*, 70:690 (1993); Driehuys B, Cates G D, Happer W, Mabuchi H, Saam B, Albert M S, and Wishnia A, *Phys Lett A*, 184:88 (1993); Long H W, Gaede H C, Shore J, Reven L, Bowers C R, Kritzenberger J, Pietrass T, Pines A, Tang P, and Reimer J A, *J Am Chem Soc*, 115:8491 (1993)). Polarized $^3$He is an important nuclear target (Anthony P L, et al., *Phys Rev Lett*, 71:959 (1993); Middleton H, PhD Thesis, Princeton University, unpublished; Newbury N R, et al., *Phys Rev Lett*, 67:3219 (1991); Newbury N R, et al., *Phys Rev Lett*, 69:391 (1992)) and has also been shown to be an excellent nucleus for gas-phase MRI (Middleton H, et al., *Magnetic Resonance in Medicine*, 33:271 (1995)).

All of these applications require that the highly non-equilibrium polarizations of the noble gas nuclei be long-lived, i.e., the decay of polarization to thermal equilibrium level must be slow. However, interactions of the polarized noble gas nuclei with surfaces can cause rapid relaxation, often resulting in relaxation times $T_1$ that are undesirably short. Understanding these mechanisms, and devising methods of inhibiting relaxation, is vital for continued progress in a large variety of experiments using polarized noble gases.

Bouchiat and Brossel identified relaxation of hyperpolarized rubidium on coatings of paraffin on the walls of glass resonance cells (Bouchiat M A, and Brossel J, *Phys Rev*, 147:41 (1996)). This relaxation was attributed to adsorption of rubidium on the coatings leading to depolarizing interactions such as dipole-dipole interaction between electron spin of the rubidium atom and the nuclear spin of the protons in the coating. This paper reported a diminution of such interactions upon substituting $(CD_2)_n$ paraffins for $(CH_2)_n$ paraffins, i.e., deuterating the paraffins. Bouchiat and Brossel, however, do not extrapolate on this work and make no inferences concerning potential interactions of other elements with paraffins. Nor does this paper indicate whether any other polymeric materials depolarize rubidium.

Zeng and co-workers made substantial progress in reducing $^{129}$Xe surface relaxation by introducing the use of a silicone coating agent (Zeng X, Miron E, van Wijngaarden W A, Schreiber D, and Happer W, *Phys Lett*, 96A:191 (1983)). Relaxation times of order $T_1$~20 min are now routinely attained using such coatings. Nonetheless, these relaxation times are still approximately two orders of magnitude shorter than what is ultimately possible for gaseous $^{129}$Xe at standard temperatures and pressures. It has been thought that continuing inability to improve nuclear spin lifetimes is attributable to paramagnetic impurities in the coating compositions. Efforts to reduce relaxation by removing such impurities, however, have met with little success. Accordingly, it is evident that better understanding of the $^{129}$Xe surface interactions has been needed.

As a result, there exists a need for improving the yield of noble gas hyperpolarization processes by reducing the depolarizing interactions of the noble gas with surfaces in the hyperpolarization system.

There is also a need for increasing the total amount of hyperpolarization in a noble gas by reducing counteracting depolarizing interactions between the noble gas and its physical environment.

Moreover, there is a need for improving the duration of storage of hyperpolarized noble gas by reducing depolarizing interactions of the noble gas with storage containers which house the gas.

In addition, there is a need for improving the efficiency of magnetic resonance imaging methods which require the use of hyperpolarized noble gas nuclei by decreasing the amount of physical interaction of the noble gas with physical systems employed for delivery of the hyperpolarized gas for imaging.

SUMMARY OF THE INVENTION

The present invention addresses the inadequacies of prior technologies by providing a method of reducing depolarizing interactions between hyperpolarized noble gas nuclei and surfaces which can adsorb and trap such nuclei.

The invention provides a method of reducing the depolarizing effect of the adsorption and trapping of noble gas nuclei, preferably $^{129}$Xe, by surfaces with which the gas comes in contact. In a preferred embodiment, the invention includes coating a surface with a modified polymer which inhibits nuclear spin relaxation. Preferably, the modified polymer is a polymer which has been modified by deuteration to replace at least some protons with deuterons. Alternatively, or in conjunction with deuteration, the polymer may be modified to reduce its permeability. Methods are known to reduce polymer permeability, including cross-linking of a polymer as well as halogenation, preferably fluorination, of a polymer.

Thus, in one embodiment, the invention provides a method of inhibiting nuclear spin relaxation of a hyperpolarized noble gas, including:

inhibiting depolarizing interaction of a hyperpolarized noble gas with a surface. In this embodiment, the method includes coating the surface with a polymer having reduced capacity for depolarizing interaction with said noble gas. Preferably, the coating exhibits reduced trapping or adsorption of the noble gas, or which limits the amount of dipole-dipole interactions between the polymer nuclei the noble gas.

The polymer coating useful according to the invention preferably includes a modified silicon-containing polymer, or a modified hydrocarbon polymer. The modified polymers are preferably deuterated, modified to reduce permeability to a noble gas, or modified by a combination of both means.

Preferred modified silicon-containing polymers include deuterated polysiloxanes, deuterated silane polymers, and combinations thereof. A highly preferred modified silicon-containing polymer is deuterated dichloro(di-methylsiloxane). Other preferred siloxanes include cross-linked siloxanes, having reduced permeability. Such polymers may also be deuterated to provide additional reduction in depolarizing capacity.

Preferred modified hydrocarbon polymers useful according to the invention include deuterated hydrocarbon polymers, and hydrocarbon polymers having modified permeability to a noble gas. The modified hydrocarbon polymer is selected from among modified paraffins, modified homopolymers or copolymers of polyolefins, and combinations thereof, provided that said polymer may be used as a coating on a surface. Hydrocarbon polymers useful according to the invention may also be cross-linked.

In another embodiment, the invention provides a method of hyperpolarizing a noble gas, wherein the method includes hyperpolarizing a noble gas in a container adapted for hyperpolarization of a noble gas, wherein the container has a surface which has been modified to exhibit reduced depolarizing interaction with the noble gas. Preferably, the surface is coated with a modified polymer such as described above and elsewhere herein.

In yet another embodiment, the invention provides a method of reducing the noble-gas depolarizing capacity of a surface of a container, wherein the method includes coating a surface of a container, adapted to receive a noble gas, with a polymer having substantially reduced capacity to depolarize the noble gas. Preferably, the surface of the container is coated with a polymer such as is described above and elsewhere herein.

Still further, the invention provides containers for noble gases in which the surfaces of the containers have been modified according to the method of the invention. Preferred containers include any container which can come in contact with, or are adapted to receive, a noble gas, either during or after hyperpolarization. Such containers include hyperpolarization cells, storage reservoirs, conduits, and the like. Typically such containers are made of a substantially impermeable material, preferably glass.

The invention also provides a method of hyperpolarizing a noble gas, wherein the method includes hyperpolarizing a noble gas in a cell modified according to the method of the invention. Moreover, the invention provides a method of storing a hyperpolarized noble gas, wherein the method includes storing a hyperpolarized noble gas in a reservoir which has been modified according to the method of the invention.

Accordingly, as a result of the invention, previous physical factors which have limited the ability to hyperpolarize noble gases and to maintain that hyperpolarization have been dramatically reduced. Consequently, applications of nuclear magnetic resonance spectroscopy, as well as magnetic resonance imaging methods, which require the use of hyperpolarized noble gases, may now be practiced with significantly enhanced efficiency. Indeed, certain applications which were previously of limited practicality are now substantially improved.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein.

DETAILED DESCRIPTION OF THE INVENTION

Figure 1:
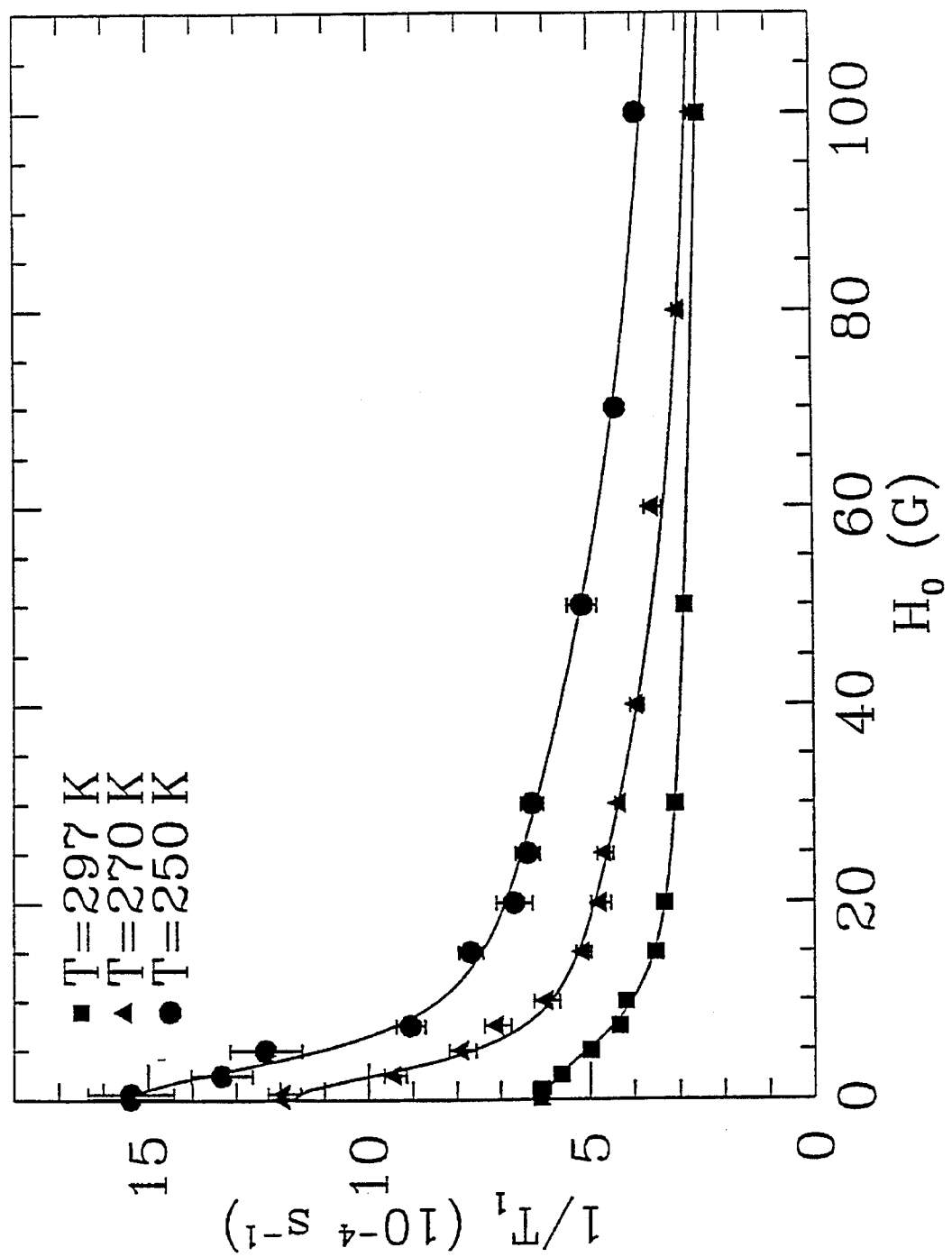
FIG. 1 illustrates representative magnetic field dependence of the nuclear spin relaxation of polarized $^{129}$Xe on a silicone coating at varied temperatures.

As noted previously herein, Zeng and co-workers made substantial progress in reducing $^{129}$Xe surface relaxation by introducing the use of a silicone coating (Zeng et al., *Phys Lett*, 96A:191 (1983)). Relaxation times of order $T_1 \sim 20$ min are now routinely attained, but are still approximately two orders of magnitude shorter than what is ultimately possible for gaseous $^{129}$Xe at 1 amagat. (1 amagat=$2.689 \times 10^{19}$ atoms/cm$^3$, the density of an ideal gas at 273K and 1 atm.) Specifically, the spin-rotation interaction $\gamma$N·I between the $^{129}$Xe nuclear spin I and the molecular angular momentum N during $^{129}$Xe—Xe collisions limits the gas-phase relaxation time to $T_1=52/\rho$ hr amagat (Hunt E R, and Cart H Y, *Phys Rev*, 130:2302 (1963); Torrey H C, *Phys Rev*, 130:2306 (1963)). In order to achieve polarization lifetimes approaching such limits, a better understanding is needed of the interactions between $^{129}$Xe and surfaces.

We have now determined that $^{129}$Xe relaxation in cells coated with a polymer such as a siloxane is not primarily a function of interaction of the xenon with paramagnetic impurities as has been conventionally thought. It is well known that paramagnetic factors such as iron and oxygen contaminants are generally highly efficient at relaxing $^{129}$Xe nuclear spin. It has been assumed that such factors dominate $^{129}$Xe relaxation by surfaces. Instead, it has surprisingly been found that the interactions of xenon with polymer surfaces can have lifetimes several orders of magnitude longer than conventional gas-surface interactions. Effectively, it is now understood that $^{129}$Xe is trapped in the surface for average periods on the order of microseconds ($10^{-6}$ sec) rather than picoseconds ($10^{-12}$ sec). As a result of this unusual phenomenon, it has now been found that the relaxation of $^{129}$Xe is primarily due to dipolar interactions with the coating protons while the $^{129}$Xe is trapped within the coating.

Because $^{129}$Xe has now been shown to relax through unexpected dipolar contact with the coating protons, it was inferred that some method of limiting such contact would reduce relaxation. One method of limiting contact would involve limiting the extent of the type of contact which would lead to depolarization. This would require removal of the moieties in the coating which cause depolarization, i.e., the protons. The principal attribute of protons responsible for depolarization of noble gas nuclei is their significant magnetic moment. Accordingly, the removal of the coating protons and their replacement with moieties having smaller magnetic moment would reduce the depolarizing influence of the coating. A preferred substituent for the protons are deuterons which have a magnetic moment which is 6.5 times smaller than the magnetic moment of protons.

The use of a deuterated surface coating to slow down the relaxation of Rubidium electron spins was demonstrated by Bouchiat in her work on alkali metal relaxation on paraffins (Bouchiat et al., *Phys Rev,* 147:41 (1996). The interactions observed by Bouchiat have time constants of order $10^{-10}$, which are strikingly shorter than durations of the trapping phenomena we have observed for xenon. Thus, extrapolation from Bouchiat is not self-evident. In fact, application of Bouchiat's conclusions to noble gas relaxation on surfaces would imply lifetimes ($T_1$) on the order of 100 years. However, measured lifetimes are up to 6 orders of magnitude smaller, an observation which supports the assumption that paramagnetic factors dominate relaxation. Thus, a replacement of protons by deuterons in such a system would be assumed to be a virtually useless exercise.

Silicone and silane polymers have achieved prominent use in the field of noble gas polarization primarily due to their ease of use. Typical of such compounds is a dichloro(dimethylsiloxane) sold under the SurfaSil™ brand name by Pierce Scientific, Inc. Deuterated silicones and silanes may be employed according to the invention to reduce nuclear spin relaxation of noble gases. The deuterated siloxanes preferably have a structure $[(-SiR^1R^2O-)_n](Cl)_2$, where n is greater than 2, preferably about 2–1000. Thus, the siloxanes include a polymer of siloxane units having substituents $R^1$ and $R^2$, which are independently deuterium or a partially or completely deuterated hydrocarbyl group, typically a partially or completely deuterated alkyl group of 1–4 carbons. It is also known to cross-link silicon polymers, such as polysiloxanes. Such modification can be accomplished separated from or in conjunction with deuteration of the polymer. Preferred siloxanes and silanes include terminal chloro groups for ease of coating onto a surface such as glass.

Such deuterated silicon compounds as deuterated siloxanes and deuterated silanes may be prepared according to known methods to provide coating polymers having improved compatibility with hyperpolarized noble gases. Typically, the preparation of deuterated silicon polymers requires deuteration prior to polymerization. For example, hydrocarbon moieties such as lower alkyl groups (R) on $SiOR^1R^2$ subunits are deuterated prior to the polymerization into a polysiloxane. Methods for preparing substituted silicon compounds are described, for example, in U.S. Pat. Nos. 3,642,851 and 3,646,090, the disclosures of which are incorporated herein by reference. Methods for cross-linking such polymers are also known.

Hydrocarbon polymers such as paraffins $((CH_2)_n)$ and polyolefins have also been employed to reduce nuclear spin relaxation of hyperpolarized noble gases on surfaces. Deuterated hydrocarbon polymers may, accordingly, be employed according to the invention to achieve even longer lifetimes for noble gas nuclei. Methods of deuterating polymers are known in the art. The deuteration of hydrocarbon polymers is described, for example, in U.S. Pat. Nos. 3,657,363, 3,966,781, 3,989,705, and 4,914,160, the disclosures of which are incorporated herein by reference. Such methods typically require catalytic substitution of deuterons for protons.

Preferred deuterated hydrocarbon polymers and copolymers include deuterated paraffins, polyolefins, and the like. Such polymers may also be cross-linked according to known methods.

Another approach to reducing spin relaxation according to the invention involves improving coating performance by decreasing its permeability to xenon. A reduction in permeability would lead to decreased xenon trapping times and, consequently, increased nuclear spin lifetimes. Methods of preparing polymers having reduced gas permeability are known in the art. For example, the halogenation, preferably the fluorination, of a polymer can decrease its permeability to xenon and other noble gases. A method for fluorinating a silicon polymer has described, for example, in a paper by LeRoux et al. which describes gas transport properties of fluorinated poly(vinyltrimethylsilane) polymers (LeRoux J D, Teplyakov V V, and Paul D R, *J Membr Sci,* 90:55 (1994)). Mohr et al. have studied gas separation properties of fluorinated poly(4-methyl-1-pentene) polymers (Mohr J M, Paul D R, Mlsna T E, and Lagow R J, *J Membr Sci,* 55:131 (1991)). The disclosures of these documents are incorporated herein by reference. Other silicon and hydrocarbon polymers may be modified in similar fashion. Moreover, other substituents may be substituted for protons to achieve similar reductions in polymer permeability, e.g., carboxylation and sulfonation (Mohr et al., *J Membr Sci,* 55:131 (1991)).

Noble gas hyperpolarization according to the method of the invention is most preferably performed using the $^{129}$Xe nucleus. However, the method of the invention may also be performed with other noble gases, i.e., other noble gas isotopes having nuclear spin. $^3$He, $^{129}$Xe and the other noble gases may be preferred in different applications because of their different physical and magnetic resonance properties. A list of noble gas nuclei useful according to the invention is provided below in Table I. This list is intended to be illustrative and non-limiting.

TABLE I

| Hyperpolarizable Noble Gases | | |
|---|---|---|
| Isotope | Natural Abundance (%) | Nuclear Spin |
| $^3$He | ~$10^{-6}$ | ½ |
| $^{21}$Ne | 0.27 | 3/2 |
| $^{83}$Kr | 11.5 | 9/2 |
| $^{129}$Xe | 26.4 | ½ |
| $^{131}$Xe | 21.2 | 3/2 |

While each of the noble gas isotopes listed in Table I, alone or in combination, may be hyperpolarized, it is known that the degree of polarization of the gases in equilibrium (Boltzmann) state is typically too low to permit certain uses such as nuclear magnetic resonance imaging using high speed image acquisition. The various parameters governing signal decay such as $T_1$ and $T_2$ relaxation and the local environment of the nucleus will also determine whether high speed images can be effectively acquired. These limitations become of great importance in acquisition of images from in vitro and in vivo biological systems since the time course of events desired to be imaged often requires data acquisition periods of less than one second. Enhancement of the NMR signal is, therefore, highly desirable. Accordingly, the noble gas is preferably hyperpolarized relative to its normal Boltzmann polarization. Such hyperpolarization is preferably induced prior to data acquisition by an NMR spectrometer and may be induced by any of the techniques known in the art.

Further enhancement of the noble gas magnetic resonance signal may be obtained, independently of or together with hyperpolarization, by increasing the proportion of the detectable isotope in each noble gas to a level above the natural abundance of such imageable isotopes in the noble gas. In the case of $^{129}$Xe, which has a natural isotopic abundance of about 26%, this amounts to enhancement by no more than a factor of four, even in a gas which is enriched to 100% $^{129}$Xe. Other considerations, such as the hyperpolarizability of the noble gas, usually play a much larger role in signal enhancement, but isotopic enrichment can provide a significant contribution to the ultimate efficacy of the present invention. This is especially true in the case of $^3$He which has a natural abundance of on the order of $10^{-6}$. Even the hyperpolarizability of $^3$He and its very large magnetic resonance signal could be considerably offset by the low natural abundance of this isotope. Despite its low natural abundance, however, $^3$He is readily available in very pure form as a result of industrial use of tritium ($^3$H), which decays exclusively to $^3$He. The ready availability of artificial sources of $^3$He eliminates concerns regarding its low natural abundance and associated expensive enrichment processes.

Nonetheless, even given the above enhancements, the invention now provides additional enhancement of NMR techniques which rely on hyperpolarization of noble gas nuclei. The extension of relaxation times enabled by the invention simply has not been possible heretofore.

Noble gases may be hyperpolarized in accordance with the invention through any of various means known in the art. Any noble gas hyperpolarization process may be employed since the effects of the invention are believed to be independent of the method by which hyperpolarization is achieved. Such methods include, for example, spin-exchange interactions with optically pumped alkali metal vapor. (Bhaskar et al., *Phys Rev Lett* 49:25 (1982); Cates G D, Fitzgerald R J, Barton A S, Bogorad P, Gatzke M, Newbury N R, and Saam B, *Phys Rev A*, 45:4631 (1992); Bouchiat M A, Carver T R, and Varnum C M, Phys Rev Lett, 5:373 (1960); Zeng X, Wu Z, Call T, Miron E, Schreiber D, and Happer W, *Phys Rev A*, 31:260 (1985)). The optical pumping and spin-exchange can be performed using modest applied magnetic fields of about 1 G or larger. Pumping in the NMR magnet bore at fields of several Tesla is also possible. The maximum steady state $^{129}$Xe nuclear polarization achievable depends on the time constant characterizing the spin exchange with the alkali metal and the time constant characterizing the relaxation ($T_1$) due, for example, to contact with the surfaces of the pumping cell. For instance, with $T_1 \approx 20$ min, polarizations of 20–40% are quite practicable, (Cates G D, Benton D R, Gatzke M, Happer W, Hasson K C, and Newbury N R, *Phys Rev Lett*, 65:2591 (1990)), and polarizations of 90% or more should be attainable. The long $T_1$ of the gas also allows samples to be manipulated, even stored as Xe ice, (Cates et al., *Phys Rev Lett*, 65:2591 (1990)), and transported on time scales of hours or even days, without serious loss of magnetization. Even so, the invention now enables further improvement of these polarizations.

The art of hyperpolarizing noble gases through spin exchange with an optically pumped alkali-metal vapor starts with the irradiation of the alkali-metal vapor with circularly polarized light at the wavelength of the first principal ($D_1$) resonance of the alkali metal (e.g. 795 nm for Rb). The $^2S_{1/2}$ ground state atoms are thus excited to the $^2P_{1/2}$ state and subsequently decay back to the ground state. If performed in a modest (10 Gauss) magnetic field aligned along the axis of incident $D_1$ light, this cycling of atoms between the ground and first excited states leads to nearly 100% polarization of the atoms in a few microseconds. This polarization is carried mostly by the lone valence electron characteristic of all alkali metals; this essentially means that all of these electrons have their spin either aligned or anti-aligned to the magnetic field depending upon the helicity (right- or left-handed circular polarization state) of the pumping light. If a noble gas with non-zero nuclear spin is also present, the alkali-metal atoms can undergo collisions with the noble gas atoms in which the polarization of the valence electrons is transferred to the noble-gas nuclei through a mutual spin flip. This spin exchange results from the Fermi-contact hyperfine interaction between the electron and the noble-gas nucleus. By maintaining the alkali-metal polarization at nearly 100% with the pumping light, large non-equilibrium polarizations (5%–80%) are currently achievable in large quantities of a variety of noble gases through this spin-exchange process. For example, one currently available Titanium:Sapphire-laser could theoretically provide 1 g/hr (200 cc-atm/hr) of highly polarized $^{129}$Xe.

The alkali metals capable of acting as spin exchange partners in optically pumped systems include any of the alkali metals. Preferred alkali metals for this hyperpolarization technique include Sodium-23, Potassium-39, Rubidium-85, Rubidium-87, and Cesium-133. Alkali metal isotopes, useful according to the invention, and their relative abundance and nuclear spins are listed in Table II, below. This list is intended to be illustrative and non-limiting.

TABLE II

Alkali Metals Capable of Spin Exchange

| Isotope | Natural Abundance (%) | Nuclear Spin |
|---|---|---|
| $^{23}$Na | 100 | 3/2 |
| $^{39}$K | 93.3 | 3/2 |
| $^{85}$Rb | 72.2 | 5/2 |
| $^{87}$Rb | 27.8 | 3/2 |
| $^{133}$Cs | 100 | 7/2 |

Alternatively, the noble gas may be hyperpolarized using metastability exchange. (Schearer L D, *Phys Rev*, 180:83 (1969); Laloe F, Nacher P J, Leduc M, and Schearer L D, AIP ConfProc #131 (Workshop on Polarized $^3$He Beams and Targets) (1984)). The technique of metastability exchange involves direct optical pumping of, for example, $^3$He, without need for an alkali metal intermediary. The method of metastability exchange usually involves the excitation of ground state $^3$He atoms ($1^1S_0$) to a metastable state ($2^3S_1$) by weak radio frequency discharge. The $2^3S_1$ atoms are then optically pumped using circularly polarized light having a wavelength of 1.08 μm in the case of $^3$He. The light drives transitions up to the $2^3P$ states, producing high polarizations in the metastable state to which the $2^3P$ atoms then decay. The polarization of the $2^3S_1$ states is rapidly transferred to the ground state through metastability exchange collisions between metastable and ground state atoms. Metastability exchange optical pumping will work in the same low magnetic fields in which spin exchange pumping works. Similar polarizations are achievable, but generally at lower pressures, e.g., about 0–10 Torr.

The magnitude of the increase in relaxation time made possible by means of the method of the invention now permits a substantial increase in the efficiency of noble gas hyperpolarization processes, as well as an increase in the efficiency and practicability of methods which depend on the use of hyperpolarized noble gases. In addition to the practical implications for improvements in polarized noble gas technology, this invention has also demonstrated that $^{129}$Xe relaxation studies can provide a unique probe of polymer surfaces or membranes in biological systems. Studies of $^{129}$Xe relaxation in a variety of environments should be of particular interest to the further development of NMR-based procedures with laser-polarized noble gases. A particularly significant procedure which can take advantage of the extended polarization lifetimes enabled by the invention is medical nuclear magnetic resonance imaging of in vitro and in vivo biological systems, such as is described in U.S. application Ser. No. 08/225,243, filed on Apr. 8, 1994, now U.S. Pat. No. 5,545,396, the entire disclosure of which is incorporated herein by reference.

The following examples are intended to assist in a further understanding of the invention. The particular materials and conditions employed are intended to be further illustrative of the invention and do not limit the reasonable scope thereof.

EXAMPLE 1

Experiments used several 1 cm$^3$ spherical Pyrex cells treated with SurfaSil™ brand coating (Pierce Scientific Inc., Rockland, Ill.) according to the method described by Zeng et al. (Zeng et al., *Phys Lett*, 96A:191 (1983)). The cells were attached to a glass manifold and connected to a vacuum system (base system pressure of P=1×10$^{-8}$ Torr). The manifold was baked out under vacuum at 150° C. for 1–2 days. Each cell contained a few mg of Rb and was filled under liquid nitrogen with roughly 0.5 amagat of isotopically enriched xenon (72.9% $^{129}$Xe) and 0.1 amagat of N$_2$, both purified by flowing through zirconium getters from Ultrapure, Inc.

In order to measure the $^{129}$Xe relaxation rates, the nuclei were first polarized to ~25% through optical pumping and spin exchange. Cells were placed in a 30 G magnetic field and heated to 85° C., increasing the Rb density to [Rb]≈2× 10$^{12}$ cm$^{-3}$. The Rb atoms were optically pumped with 2–4 W of circularly polarized 795 nm Rb D$_1$ light from a Ti:Sapphire laser, while polarization of the $^{129}$Xe nuclei proceeded through Rb-Xe spin-exchange collisions (Happer et al., *Phys Rev A* 29:3092 (1984); Cates et al., *Phys Rev A*, 45:4631 (1992)). After ~20 min. the cells were removed from the pumping oven and cooled to room temperature. Cells were then placed in a cryostat (77–300 K) in a Helmholtz pair, variable in field from 0–2000 G. For the double resonance experiments, the magnetic field was locked and stabilized near 97 G using an optically pumped $^{85}$Rb magnetometer (Newbury N K, Barton A S, Bogorad P, Cates G D, Gatzke M, Mabuchi H, and Saam B, *Phys Rev A*, 48:558 (1993)).

The $^{129}$Xe polarization decay was monitored by Adiabatic Fast Passage NMR (AFP) (Abragam A, *Principles of Nuclear Magnetism*, pp. 65–68 and 264–98, Oxford University Press, New York (1961)) which allows the magnetization to be detected with negligible loss of polarization. A field H$_1$, rotating at a frequency ω$_0$, was first applied perpendicular to the static field H$_0$. The static field was then swept slowly through the NMR resonance condition ω$_0$=7402 s$^{-1}$G$^{-1}$H$_0$, inverting the entire magnetization as we detected the transverse component with a tuned pick-up coil and lock-in amplifier. The decay of AFP signal height versus time was fit to an exponential to determine the longitudinal relaxation time T$_1$ or spin locked relaxation time T$_{1\rho}$ (Hartmann S R and Hahn E L, *Phys Rev*, 128:2042 (1962)). Spin locking of the $^{129}$Xe was achieved by stopping the field sweep exactly on resonance when the magnetization is aligned with H$_1$ in the frame rotating at ω$_0$. During $^{129}$Xe spin locking, a second rf field was applied at the proton resonance frequency to slow the $^{129}$Xe relaxation rate.

EXAMPLE 2

FIG. 1 shows the static magnetic field dependence of the $^{129}$Xe relaxation rate at a variety of temperatures. Interpretation of these data required development of the following model. During a coating dwell time $\tau_d$ the $^{129}$Xe nuclear spin I can couple to a neighboring electronic or nuclear spin S through dipolar interactions. To reduce the complexity of the model, the tensor properties of the dipolar coupling were ignored and the interaction was taken to be a scalar coupling $\mathcal{H}=\hbar$ AI·S. The analysis is qualitatively the same with scalar or tensor coupling. The field-dependent $^{129}$Xe relaxation rate, calculated to first order (Abragam, *Principles of Nuclear Magnetism*, pp. 65–68 and 264–98, Oxford University Press, New York, (1961)), is $$\frac{1}{T_1} = \frac{2A^2}{3} \frac{\tau_d}{\tau_d + \tau_g} S(S+1) \frac{\tau_d}{1+(\omega_{0I}-\omega_{0S})^2\tau_d^2}, \quad (1)$$

where the ratio $\tau_d/(\tau_d+\tau g)$ reflects the time $\tau_d$ a given $^{129}$Xe spends adsorbed on the surface compared to its time in the gas phase $\tau_g$ and ω$_{0I}$ and ω$_{0S}$ are the resonance frequencies of the $^{129}$Xe spin and the surface spin respectively. Using Equation (1) and the measured half width ΔH≈8 G of the relaxation curve, an estimate of the $^{129}$Xe dwell time was made under various assumptions about the size of the surface magnetic moment. Specifically, for $^{129}$Xe surface relaxation by paramagnetic sites, it was found that $\tau_d$=7 nanoseconds (ns), whereas for $^{129}$Xe-proton relaxation, it was found that $\tau_d$=4 microseconds (μs). This three order of magnitude difference in dwell times is due to the much larger electron magnetic moment compared to that of the proton ($\mu_B/\mu_N$~1800). While a 7 ns surface adsorption time is conceivable, the 4 μs estimated for the proton interaction would appear to require that $^{129}$Xe be trapped within the coating rather than being merely adsorbed on its surface. To distinguish between these two vastly different regimes, i.e., paramagnetic surface relaxation versus proton dipolar relaxation, studies were made of the temperature dependence of the relaxation parameters.

EXAMPLE 3

Figure 2:
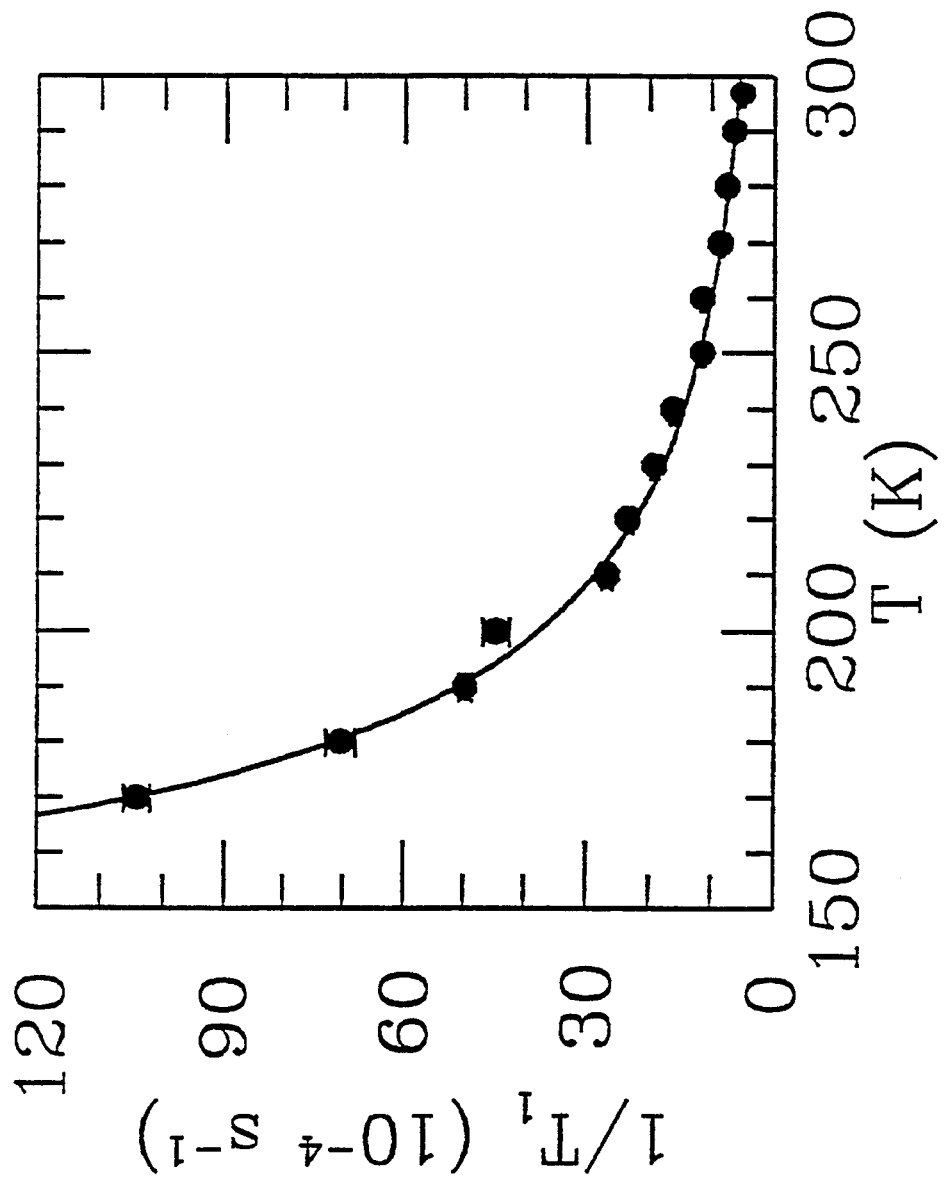
FIG. 2 illustrates the exponential temperature dependence of the $^{129}$Xe relaxation rate resulting from increasing solubility of xenon in the coating.

The temperature dependence data we obtained are not consistent with $^{129}$Xe simply being adsorbed on the surface. The $^{129}$Xe surface adsorption time is dependent on adsorption energy E$_\alpha$ and temperature through $$\tau_d = \tau_0 e^{E_\alpha/kT}, \quad (2)$$

with $\tau_0 \approx 10^{-12}$ s. As the temperature is lowered and $\tau_d$ becomes longer, Equation (1) implies an increased zero-field relaxation rate and narrowing of the field-dependence. The measured temperature dependence of the zero-field relaxation rate is shown in FIG. 2 and it is indeed exponential. Using Equations (1) and (2) and assuming $\tau_g \gg \tau_d$, it was found that $1/T_1(B_0=0) \propto \tau_0^2 \exp(2E_\alpha/kT)$, yielding an adsorption energy $E_\alpha=0.05\pm0.003$ eV. However, the 7 ps dwell time calculated for T=297 K using this adsorption energy is far too short to be consistent with the observed width of the field dependence. Moreover, the width of the relaxation curve is independent of temperature, in further contradiction to the expected narrowing from increased $^{129}$Xe surface dwell time at lower temperatures. It was, therefore, necessary to consider the possibility of xenon trapping in the coating for the microsecond time scales which would be needed for proton dipolar interactions to cause the observed effects.

While microsecond-long trapping times were unexpected, xenon is known to be soluble in certain polymer systems (Miller J B, *Rubber Chem and Tech*, 66:455 (1993)), and work by Wu and co-workers on $^{131}$Xe relaxation in silicone coated cells is also suggestive of Xe entering the bulk of the polymer (Wu Z, Happer W, Kitano M, and Daniels J., *Phys Rev A*, 42:2774 (1990)). The exponential temperature dependence of the zero-field relaxation rate (FIG. 2) may result from the temperature-dependent solubility of Xe in the coating (Pollack G L, Kennan R P, Himm S F, and Carr P W, *J Chem Phys*, 90:6569 (1989)), characterized by a heat of solution $\Delta H_{sol}=-0.10\pm0.005$ eV. The microsecond $^{129}$Xe correlation times which are required if the magnetic decoupling of FIG. 1 is due to nuclear dipole-dipole interactions imply that there must be an energy barrier $E_b$>kTln(1 μs/1 ps)≈0.5 eV, which hinders the motion of a xenon atom from one solvation site to another.

While the $^{129}$Xe remains trapped within the polymer, nuclear spin relaxation is caused by fluctuations of the local proton dipole field $H_p$ at or near the $^{129}$Xe resonance frequency. Such fluctuations could have a variety of sources, including polymer chain motions, $^{129}$Xe diffusion within the coating, or proton spin-spin interactions (Cain E J, et al., *J Phys Chem* 94:2128 (1990)). We assumed that the interactions can be characterized by correlation functions $<H_p(t)H_p(t+\tau)>=H_p^2 c^{(-|t|/\tau_c)}$ where $\tau_c$ is the characteristic time scale of the fluctuations. Taking into account the tensor nature of the dipole-dipole interaction, the $^{129}$Xe dipolar relaxation rate, analogous to Equation (1) was found to be $$\frac{1}{T_1} = \left\{ \frac{1}{1+(\omega_{0I}-\omega_{0S})^2\tau_c^2} + \frac{3}{1+\omega_{0I}^2\tau_c^2} + \frac{6}{1+(\omega_{0I}+\omega_{0S})^2\tau_c^2} \right\}, \quad (3)$$

(Abragam, *Principles of Nuclear Magnetism*, pp. 65–68 and 264–98, Oxford University Press, New York, (1961)) where $\omega_{0I}$ and $\omega_{0S}$ are the $^{129}$Xe and proton resonance frequencies, respectively, and $1/T_0$ is the zero-field relaxation rate given by $$\frac{1}{T_0} = \frac{4}{3} \frac{\tau_d}{\tau_d+\tau_g} S(S+1)\gamma_I^2\gamma_S^2\hbar^2 \tau_c \sum_i r_i^{-6} \quad (4)$$

Here $\gamma_I$ and $\gamma_S$ are the $^{129}$Xe and proton gyromagnetic ratios, and the $r_i$ are the distances to the neighboring protons. To fit the magnetic field dependence data requires the sum of at least two expressions of the form of Equation (3), each with its own magnitude and correlation time. The room-temperature correlation times inferred from measurements of three different cells are $\bar{\tau}_a=8.1\pm1.0$ μs and $\bar{\tau}_b=0.5\pm0.1$ μs, with the 8 μs component contributing roughly two thirds of the zero-field relaxation rate.

EXAMPLE 4

It has now been determined for the first time that dipolar coupling of the magnetic moments of the coating protons and the $^{129}$Xe nuclei is the dominant cause of relaxation. This was accomplished by observing a proton-$^{129}$Xe double resonance signature. As is typical of double resonance, our experiment involved spin locking the $^{129}$Xe magnetization to a resonant rotating field $H_{1I}$ while a separate field $H_{1S}$ is applied to the protons (Hartmann et al., *Phys Rev*, 128:2042 (1962)). Then the $^{129}$Xe and proton Zeeman energies were quantized independently along their respective resonant fields, allowing us to affect the $^{129}$Xe relaxation rate by manipulating only the proton spins. Despite a vast body of literature on double resonance NMR, no previous analysis of relaxation appropriate to this experiment has been found. Therefore, a new equation was required to be derived to represent the spin locked $^{129}$Xe relaxation rate under double resonance:

$$\frac{1}{T_{1\rho}} = \frac{1}{T_0} \sum_{\mu\nu\lambda} \frac{[d^1_{I\mu}(\beta_I)]^2 [d^1_{\nu\lambda}(\beta_S)]^2 C^2 (121;\nu,\mu-\nu)}{1+(\nu\omega_S-\mu\omega_I-\Omega_I+\lambda\Omega_S)^2\tau_c^2} \quad (5)$$

In Equation (5), the sums over μ, ν, and λ run from −1 to 1; the $d^1_{I\mu}$ and $d^1_{\nu\lambda}$ are Wigner d functions; C(121;ν,μ,−ν) are Clebsch-Gordan coefficients (Rose M E, *Elementary Theory of Angular Momentum*, pp. 32–75 John Wiley and Sons, Inc, New York (1957)); and $1/T_0$ is the zero-field relaxation rate of Equation (4). The angle β is a measure of the relative detuning from resonance of the $^{129}$Xe or proton rf, given by $\tan\beta_I=\omega_{1I}/(\omega_{0I}-\omega_I)$, where $\omega_{0I}$ is the Larmor frequency and $\omega_I$ is the frequency of the rf. The Larmor frequency in the $^{129}$Xe rotating coordinate system is given by $\Omega^2_I=(\omega_{0I}-\omega_I)^2+\omega^2_{1I}$, where $\omega_{1I}=\gamma_I H_{1I}$, and likewise for the protons.

The essence of this experiment can be seen by considering two dominant terms from Equation (5) and assuming exact proton and $^{129}$Xe resonance. Then Equation (5) reduces to $$\frac{1}{T_{1\rho}} = \frac{1}{10T_0} \left[ \frac{1}{1+(\omega_{1I}+\omega_{1S})^2\tau_c^2} + \frac{1}{1+(\omega_{1I}-\omega_{1S})^2\tau_c^2} + \ldots \right] \quad (6)$$

where the [. . . ] represents the 22 remaining terms which are dependent on the static field but are only weakly dependent on the fields $H_{1I}$ and $H_{1S}$. Inspection of Equation (6) reveals that the $^{129}$Xe spin locked relaxation rate can be slowed down by increasing the strength of the proton rf field $H_{1S}$. When the strength of the applied rf field $H_{1S}$ causes proton Rabi precession faster than the intrinsic frequency of the proton dipolar fluctuations ($\tau_S H_{1S}>1/\tau_c$), the $^{129}$Xe relaxation rate is reduced.

Due to the long $^{129}$Xe relaxation times and relatively infrequent coupling between a given $^{129}$Xe and coating protons, extremely long spin locking times are required, of order 100 s or more, to observe the proposed double resonance effect. During such long spin locking times, competing relaxation mechanisms from rf and static field inhomogeneities can add significantly to the relaxation rate, effects that were thoroughly investigated by Cates and co-workers (Cates G D, et al., *Phys Rev A*, 38:5092 (1988); Cates G D, Schaefer S R, and Happer W, *Phys Rev A*, 37:2877 (1988)). The results of Cates et al. can be greatly simplified for the experimental conditions herein, and the resulting inhomogeneity contribution to the spin-locked $^{129}$Xe relaxation rate is $$\frac{1}{T'_{1\rho}} = D\left[ \frac{|\nabla H_{0z}|^2}{H_1^2} + \frac{|\nabla H_1|^2}{H_1^2} \right] \quad (7)$$

where D is the xenon diffusion coefficient, $|\nabla H_{0z}|$ is the $\hat{z}$ component of the static field inhomogeneity, and $|\nabla H_1|$ is the inhomogeneity of the rf field. Since $\nabla H_1 \propto H_1$, the second term in Equation (7) is independent of $H_1$ and, therefore, for sufficiently large $H_1$, dominates the relaxation rate. At the spin locking field of 97 G the static field inhomogeneity of our apparatus was $|\nabla H_{0z}|=19.0$ mG/cm, so that this condition was met whenever $H_1 > 500$ mG. The remaining relaxation time due to $|\nabla H_1|$ was $T_{1\rho}=600$ s.

Figure 3:
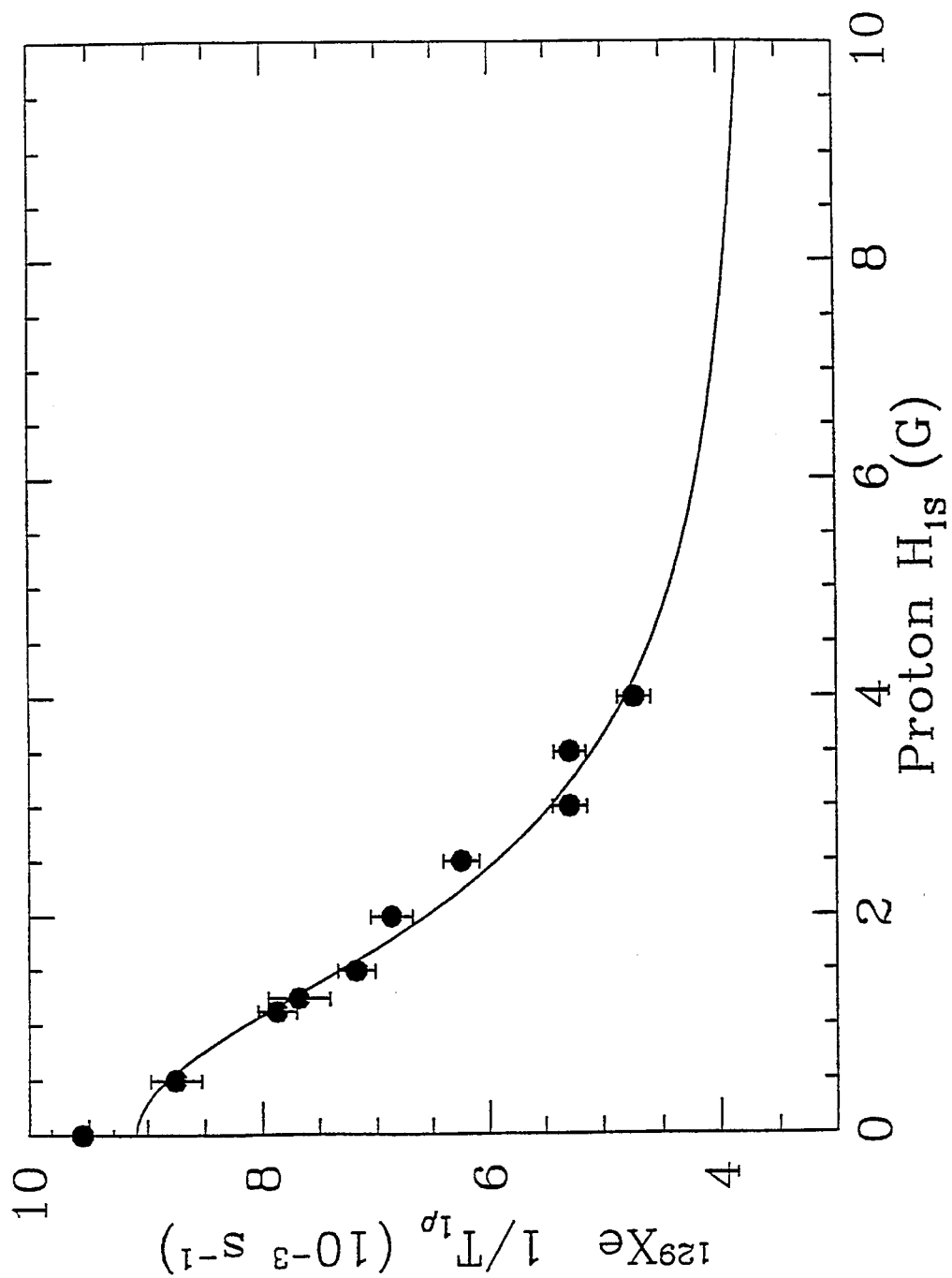
FIG. 3 illustrates resonant decoupling of the spin locked $^{129}$Xe relaxation rate $1/T_{1\rho}$ with $H_{1f}=1.1$ G.
Figure 4:
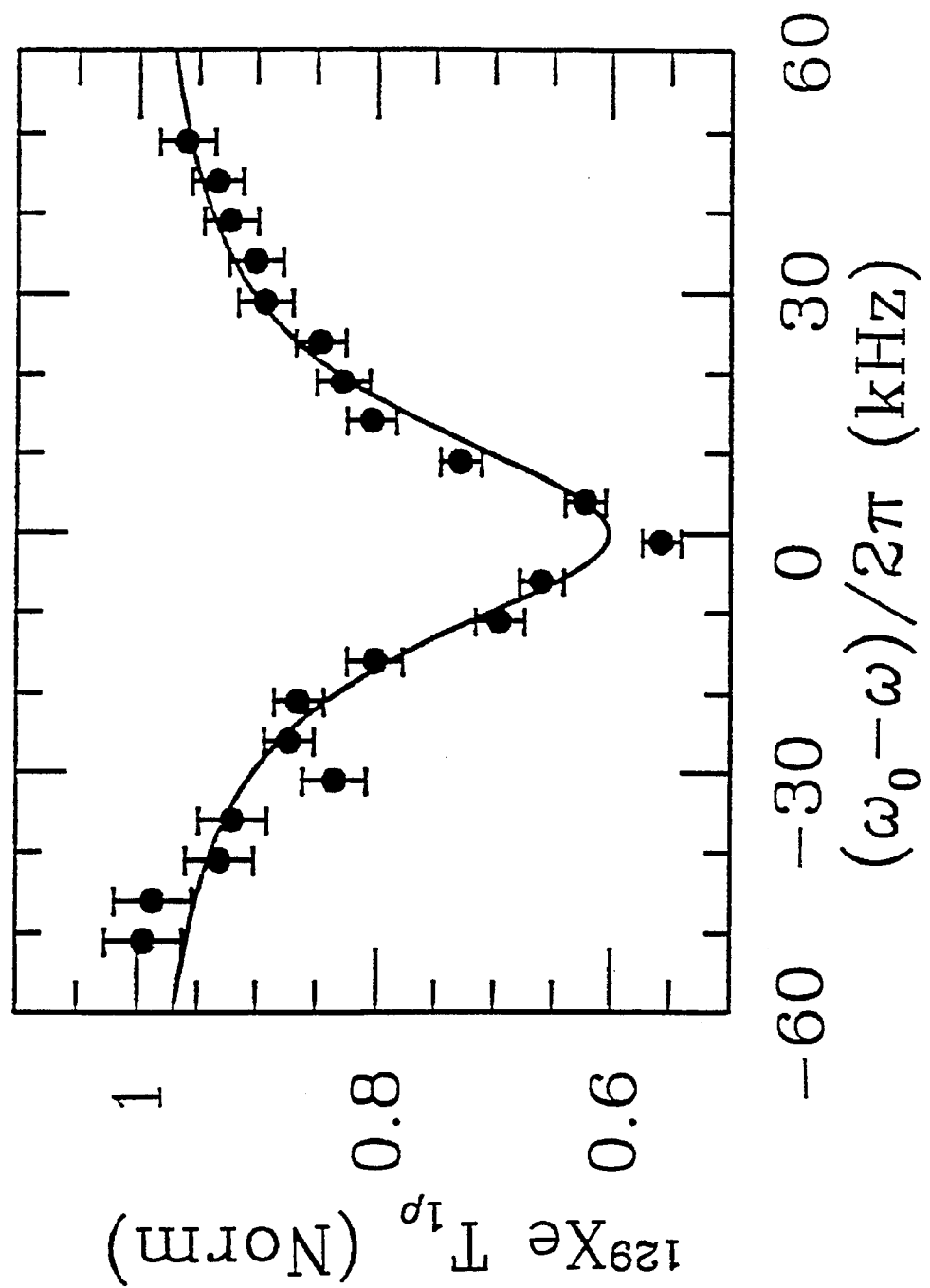
FIG. 4 illustrates the dependence of $^{129}$Xe relaxation rate on proton detuning.

FIG. 3 shows the slowing of the spin locked $^{129}$Xe relaxation rate as a function of the resonant proton field strength $H_{1S}$ at 297 K. FIG. 4 shows that the slowing is dependent on detuning from the proton resonance with a width dominated by $H_{1S}$. The resonance curve was obtained with a constant proton field strength $H_{1S}=4$ G while the frequency was varied. Maximum slowing was found to occur when the proton rf was exactly on resonance. This signature unmistakably demonstrates that dipolar relaxation in the bulk of the coating is the cause of $^{129}$Xe surface relaxation and confirms the surprisingly long trapping times of the xenon in the coating.

We note that fitting the $H_{1S}$ dependence to Equation (6) yields a correlation time $\tau_a \alpha = 17$ μs, twice as long as $\tau_\alpha = 8.1$ μs expected from the static field dependence. The magnitude of the spin locked $^{129}$Xe relaxation rate is also about 2.5 times larger than expected from the static field fit parameters and Equation (6). While these discrepancies have little effect on our basic conclusions, it is believed that our models are not yet of sufficient accuracy to permit rigorous assessment of the polymer dynamics which give rise to the relaxation.

EXAMPLE 5

At low magnetic fields, the relaxation rate of $^{129}$Xe dissolved in a polymer coating is given by $$\frac{1}{T_1} = \frac{4}{3} S(S+1)\gamma_{Xe}^2 \gamma_S^2 \hbar^2 \tau_c \sum_i r_i^{-6} \quad (8)$$

where S is the spin of the polymer nuclei, $\gamma_{Xe}$ is the gyromagnetic ratio of $^{129}$Xe, $\gamma_S$ is the gyromagnetic ratio of the polymer nuclei, $\tau_c$ is the correlation time of their interaction, and $r_i$ are the distances between the $^{129}$Xe and the surrounding polymer nuclei (Abragam, *Principles of Nuclear Magnetism*, pp 65–68 and 264–98, Oxford University Press, New York, (1961)).

Most polymers are composed of carbon, oxygen and hydrogen, or, in the case of silicones and silanes, silicon, carbon, oxygen, and hydrogen. Of these elements, the one which dominates in the relaxation of $^{129}$Xe is now understood to be hydrogen. Hydrogen is problematic not only because it is the most abundant element of most of the polymers, it is also the only element which has non-zero nuclear spin for the 100% abundant isotope. It is non-zero nuclear spin which gives rise to the nuclear magnetic moment capable of relaxing the $^{129}$Xe. As a technical detail, it must be understood that other isotopes possess non-zero spin, including $^{29}$Si (only 5% abundant), $^{13}$C (only 1% abundant), and $^{17}$O (less than 0.1% abundant). It was estimated that replacement of hydrogen by a moiety having a smaller magnetic moment could significantly reduce relaxation of the noble gas.

According to our estimates, deuterium could reduce $^{129}$Xe relaxation rate since the gyromagnetic ratio for deuterium ($\gamma_D = 4106$ s$^{-1}$G$^{-1}$) is much smaller than that of hydrogen ($\gamma_H = 26750$ s$^{-1}$G$^{-1}$). Application of these values through Equation (8), implies that the ratio of $^{129}$Xe relaxation rates in a deuterated polymer to an otherwise identical protonated polymer is $$\frac{1/T_1^D}{1/T_1^H} = \frac{1(1+1)(4106)^2}{(1/2)(1/2+1)(26750)^2} = 0.063. \quad (9)$$

In other words, the polarization lifetime of the $^{129}$Xe in the deuterated polymer would be roughly 16 times longer than in the protonated polymer.

Experimental verification of Equation (9) requires measurement of the $^{129}$Xe relaxation rates in identical vessels whose only difference is that one has been coated with a deuterated siloxane polymer, while the other is coated with protonated polymer. The procedure is as follows:

Identical Pyrex® glass spheres of roughly 1 cm$^3$ volume are coated according to conventional methods with the polymers of interest: three cells with deuterated coating and three with protonated coating. Once the coating is applied the cells are attached to a glass manifold, and baked under vacuum at 100°–150° C. for 2 days. After the bake-out, several milligrams of natural rubidium metal are distilled into each cell. The cells are then filled with approximately 1 atm of $^{129}$Xe and 70 torr of Nitrogen gas. Finally, the cells are sealed off using a hand torch.

The $^{129}$Xe is polarized by standard optical pumping (Happer W, and van Wijngaarden W A, *Hyp Int*, 38:435 (1987)) and spin exchange (Cates et al., *Phys Rev A*, 45:4631 (1992)) techniques. The cell containing polarized $^{129}$Xe is then removed from the optical pumping apparatus to a nuclear magnetic resonance (NMR) apparatus, and the relaxation rates $1/T_1$ are measured.

The size of the NMR signals are proportional to the polarization of the $^{129}$Xe. The rate of polarization decay in the sample can be measured by taking NMR signals at appropriate intervals. The NMR signal as a function of time follows exponential decay $$S(t) = S_0 e^{-t/T_1} \quad (10)$$

The decay rate of $1/T_1$ of the $^{129}$Xe polarization can be determined by fitting the NMR signal heights as a function of time to Equation (10).

The measured relaxation rates for the three deuterated samples are up to 16 times longer than for the protonated samples. As has been described in greater detail above, a 16-fold improvement in relaxation rate $1/T_1$ is the apparent theoretical limit of improvement. Due to practical limitations such as variability in coatings, it is unlikely that such an exact relationship is found. Previous polarization techniques yield lifetimes that typically range from $T_1 = 20$ to $T_1 = 40$ minutes. Such variability is suspected to stem from slight structural differences in the coatings of different cells. However, even with a factor of 2 variability arising through such causes, the factor of 16 difference in expected relaxation rates is easily discernable.

EXAMPLE 6

An experiment is performed substantially as described in Example 5, but for the comparison of a protonated polymer with a fluorinated polymer prepared according to known methods. An increase in the lifetime of hyperpolarized $^{129}$Xe of up to 16-fold is observed.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method of inhibiting nuclear spin relaxation of a hyperpolarized noble gas, comprising:

coating a surface with a polymer modified by deuteration and/or modified to have reduced permeability to the hyperpolarized noble gas when applied to the surface, thereby inhibiting depolarizing interaction of the hyperpolarized noble gas with the surface.

2. The method of claim 1, wherein said method includes inhibiting depolarizing interaction of hyperpolarized $^{129}$Xe with said surface.

3. The method of claim 1, wherein said modified polymer comprises a deuterated silicon-containing polymer.

4. The method of claim 3, wherein said silicon-containing polymer comprises a deuterated polysiloxane, a deuterated silane polymer, or a combination thereof.

5. The method of claim 4, wherein said silicon-containing polymer comprises a deuterated dichloro(dimethylsiloxane).

6. The method of claim 1, wherein said modified polymer comprises a deuterated hydrocarbon polymer.

7. The method of claim 1, wherein said modified polymer comprises a cross-linked polymer.

8. The method of claim 7, wherein said modified polymer comprises a cross-linked polysiloxane.

9. The method of claim 1, wherein said modified polymer comprises a polymer modified to include a permeability-reducing substituent.

10. The method of claim 9, wherein said modified polymer comprises a fluorinated hydrocarbon or silicon-containing polymer.

11. A method of hyperpolarizing a noble gas, comprising hyperpolarizing a noble gas in a container having a surface which has been modified to exhibit reduced depolarizing interaction with said noble gas, wherein said surface is coated with a polymer modified by deuteration and/or modified to have reduced permeability to the hyperpolarized noble gas when applied to the surface.

12. The method of claim 11, wherein said method includes hyperpolarizing $^{129}$Xe in a container having a surface which has been modified to exhibit reduced depolarizing interaction with said $^{129}$Xe.

13. The method of claim 11, wherein said modified polymer comprises a polymer modified to include a permeability-reducing substituent.

14. The method of claim 11, wherein said modified polymer comprises a deuterated silicon-containing polymer.

15. The method of claim 14, wherein said silicon-containing polymer comprises a deuterated polysiloxane, a deuterated silane polymer, or a combination thereof.

16. The method of claim 15, wherein said silicon-containing polymer comprises a deuterated dichloro(dimethylsiloxane).

17. The method of claim 11, wherein said modified polymer comprises a deuterated hydrocarbon polymer.

18. The method of claim 11, wherein said modified polymer comprises a cross-linked polymer.

19. The method of claim 18, wherein said modified polymer comprises a cross-linked polysiloxane.

20. The method of claim 13, wherein said modified polymer comprises a fluorinated hydrocarbon or silicon-containing polymer.

21. A method of reducing the noble-gas depolarizing capacity of a surface of a container, comprising:

coating a surface of a container, adapted to receive a noble gas, with a polymer modified by deuteration and/or modified to have reduced permeability to the hyperpolarized noble gas when applied to the surface, thereby providing the surface with reduced capacity to depolarize said noble gas.

22. The method of claim 21, wherein said container comprises a cell adapted for the hyperpolarization of said noble gas.

23. The method of claim 21, wherein said container comprises a reservoir adapted for the storage of a hyperpolarized noble gas.

24. The method of claim 21, wherein said modified polymer contains substantially no protons capable of depolarizing interaction with said noble gas.

25. The method of claim 21, wherein said modified polymer comprises a deuterated silicon-containing polymer.

26. The method of claim 25, wherein said silicon-containing polymer comprises a deuterated polysiloxane, a deuterated silane polymer, or a combination thereof.

27. The method of claim 26, wherein said silicon-containing polymer comprises a deuterated dichloro(dimethylsiloxane).

28. The method of claim 21, wherein said modified polymer comprises a deuterated hydrocarbon polymer.

29. The method of claim 21, wherein said modified polymer comprises a cross-linked polymer.

30. The method of claim 29, wherein said modified polymer comprises a cross-linked polysiloxane.

31. The method of claim 21, wherein said modified polymer comprises a polymer modified to include a permeability-reducing substituent.

32. The method of claim 31, wherein said modified polymer comprises a fluorinated hydrocarbon or silicon-containing polymer.

33. The method of claim 21, wherein said method includes coating a surface of a container, adapted to receive $^{129}$Xe, with a polymer having substantially reduced capacity to depolarize said $^{129}$Xe.

34. A container having reduced capacity for depolarization of a noble-gas, modified according to a method comprising:

coating a surface of a container, adapted to receive a noble gas, with a polymer modified by deuteration and/or modified to have reduced permeability to the hyperpolarized noble gas when applied to the surface, thereby providing the surface with reduced capacity to depolarize said noble gas.

35. The container of claim 34, wherein said container comprises a cell adapted for hyperpolarization of a noble gas.

36. The container of claim 34, wherein said container comprises a reservoir adapted for the storage of a noble gas.

37. The container of claim 34, wherein said polymer contains substantially no protons capable of depolarizing interaction with a noble gas.

38. The container of claim 34, wherein said modified polymer comprises a deuterated silicon-containing polymer.

39. The container of claim 38, wherein said silicon-containing polymer comprises a deuterated polysiloxane, a deuterated silane polymer, or a combination thereof.

40. The container of claim 39, wherein said silicon-containing polymer comprises a deuterated dichloro(dimethylsiloxane).

41. The container of claim 34, wherein said modified polymer comprises a deuterated hydrocarbon polymer.

42. The container of claim 34, wherein said modified polymer comprises a cross-linked polymer.

43. The container of claim 42, wherein said modified polymer comprises a cross-linked polysiloxane.

44. The container of claim 34, wherein said modified polymer comprises a polymer modified to include a permeability-reducing substituent.

45. The container of claim 44, wherein said modified polymer comprises a fluorinated hydrocarbon or silicon-containing polymer.

46. A method of hyperpolarizing a noble gas, comprising hyperpolarizing a noble gas in a cell, adapted for hyperpolarization of a noble gas, wherein an interior surface of the cell is coated with a polymer modified by deuteration and/or modified to have reduced permeability to the hyperpolarized noble gas when applied to the surface, thereby providing the surface with reduced capacity to depolarize said noble gas.

47. A method of storing a hyperpolarized noble gas, comprising storing a hyperpolarized noble gas in a reservoir, adapted for storage of a noble gas, wherein an interior surface of the reservoir is coated with a polymer modified by deuteration and/or modified to have reduced permeability the hyperpolarized noble gas when applied to the surface, thereby providing the surface with reduced capacity to depolarize said noble gas.

* * * * *